United States Patent [19]

Hernandez

[11] 4,038,755
[45] Aug. 2, 1977

[54] INTRA-ORAL WIRE BENDING PLIERS

[76] Inventor: Joseph L. Hernandez, 1972 Hopi, Santa Fe, N. Mex. 87501

[21] Appl. No.: 609,524

[22] Filed: Sept. 2, 1975

[51] Int. Cl.² .............................................. A61C 7/00
[52] U.S. Cl. ...................................................... 32/66
[58] Field of Search ................ 81/415, 416, 417, 418, 81/428; 140/104, 106; 72/909; 32/14, 66

[56] References Cited

U.S. PATENT DOCUMENTS

| 1,108,493 | 8/1914 | Federspiel | 32/66 |
| 3,144,793 | 8/1964 | Smith | 81/418 |
| 3,804,132 | 4/1974 | Mann | 32/66 |

Primary Examiner—Robert Peshock
Attorney, Agent, or Firm—Paul D. Gaetjens

[57] ABSTRACT

The pliers of this invention are specifically designed to make "first order," that is, bending in and out, or "second order," that is, stepping up or down, bends in the arch wire of an orthodontic patient without removing the arch wire from the patient's mouth. The essential feature of this device is the beveled jaws of the pliers, which allow this intra-oral arch wire adjustment.

2 Claims, 8 Drawing Figures

4,038,755

INTRA-ORAL WIRE BENDING PLIERS

BACKGROUND OF THE INVENTION

1. Field of the Invention

This invention is concerned with the intra-oral adjustment of an arch wire which is secured to the bands or brackets, which are in turn secured to the teeth in an orthodontic program. The two pliers are usually used as a set or in some instances can be used individually in accomplishing either a first order or second order bend in the arch wire while keeping the wire secured in the mouth. This allows the orthodontist to make an adjustment on the arch wire without removing it from the mouth, thus saving valuable time. A second feature of the orthodontic pliers of this invention is a set screw adjustment mounted in the upper jaw of the pliers which allows the orthodontist to adjust the amount of bend in the arch wire by controlling the amount of closure between the jaws of the pliers.

2. Prior Art

The invention disclosed in U.S. Pat. No. 3,804,132, entitled "Bow Forming Pliers," by Henry Mann, pertains to a parallel jaw plier having a pair of wire cutters manipulated by the opening and closing of the handles. The jaws of the plier are operated in a parallel manner to move complementary configurations formed in the jaws whereby the ends of the wire may be bent into closed or open loops or bayonet stops to provide a precise configurations and a series of like sized loops in the wire. The jaws are so constructed that the wire which is to be bent may be made as an offset bend or bayonet stop or a start of the bow. The jaws are particularly adapted so that wires may be formed into an outer bow loop which may be either a closed or open loop.

In U.S. Pat. No. 3,774,306, entitled "Multiple Purpose Orthodontic Pliers," by Richard W. Dobyns, there is disclosed a plier having three distinct surface curvatures on each mating surface. The pliers are particularly helpful for adjusting a crozat orthodontic appliance. During such an adjustment a particular mating pair of opposing plier surfaces is utilized to apply pressure to a particular curved section of the crozat appliance. Each of the curved surfaces of the pliers are arranged to mate perfectly with a particular curved surface of the appliance in order to perform the desired adjustment manipulation.

In U.S. Pat. No. 3,781,993 entitled "Light Wire Pliers for Orthodontists," by Anthony J. Cusato, there is disclosed a pliers for the making of very small helical and vertical loops. Inserted hardened high speed steel facing portions are fixed, as by soldering, to stainless steel jaw members of the pliers so as to face the jaws so that those extremely small size jaw ends may be used to form the wire without bending, deformation, wear or breaking of these jaw portions.

SUMMARY OF THE INVENTION

This set of two pliers are designed to make first order and second order bends in the arch wire of an orthodontic patient by means of a beveled jaw having a male and female portion, said bevel being at an approximate 45° angle and extended from the tip of the jaw near the throat of the pliers. Adjacent to the throat of the pliers is a platform area upon which impinges a set screw which determines the amount of closure of the jaws of the pliers. The purpose of the set screw is to allow the orthodontist the flexibility to determine the amount of bend in the arch wire. With the set screw in a withdrawn mode, a maximum bend is made, and as the screw is further inserted, a lesser bend is achieved.

DESCRIPTION OF THE PREFERRED EMBODIMENT

Figure 1:
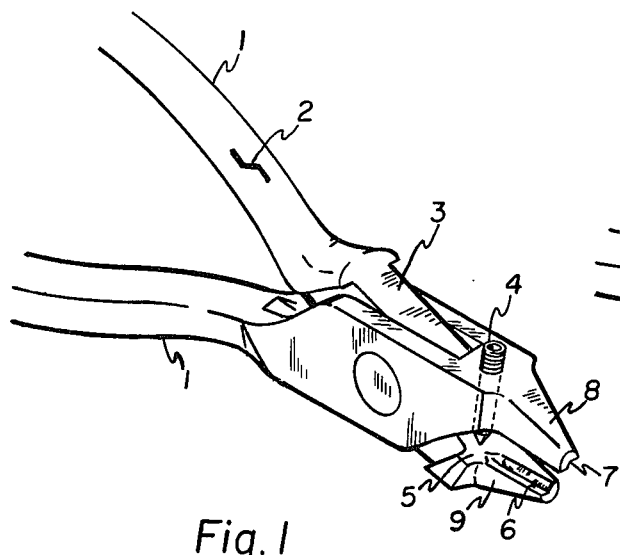
FIG. 1 is an isometric view of one set of pliers showing the beveled surface of the jaw and the set screw adjustment.

In FIG. 1 we have shown a pliers 1 which can perform a second order bend in a step up position in the arch wire in the patient. The symbol 2 indicates that this is a step up bend and is engraved or a suitable decal is placed on the handle so that the dentist can tell immediately the type of bend the said pliers will perform. The pliers 1 is similar to other orthodontic pliers in that it has a pair of jaws which pivot in a normal fashion, but is unusual in its construction in that the jaw 8 contains male bevel portion 7 and female bevel portion 6, said bevels being at an approximate 45° angle. A further novelty of this pliers is a set screw 4 which impinges on the throat of the pliers which has a platform 5, thus allowing the orthodontist the flexibility to determine the amount of bend he wants in the arch wire 11.

Figure 2:
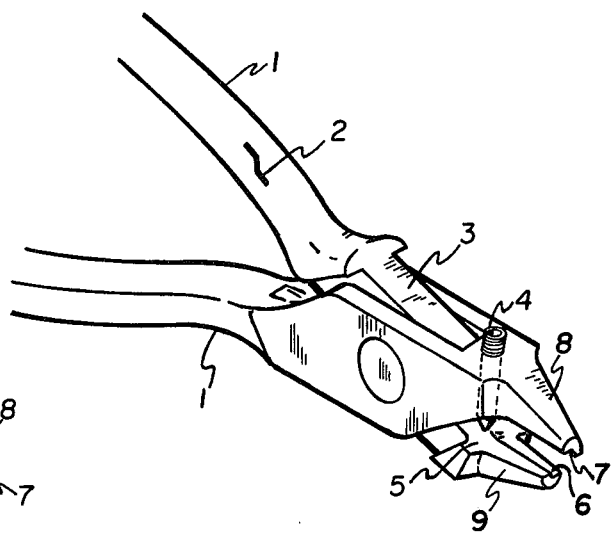
FIG. 2 is an isometric view showing the complementary pliers which make up the set of two pliers which constitute this invention.

FIG. 2 shows the second configuration of the pliers necessary to make a step down bend in the arch wire. It is to be understood that this invention is contained in a set of these pliers, namely, the pliers of FIG. 1 and FIG. 2. The step down pliers is similar to the pliers of FIG. 1 with the exception that the bevel surface is on the opposite side of the jaws as shown by callout 9.

USE OF THE PLIERS OF FIGS. 1 AND 2

Figure 3A:
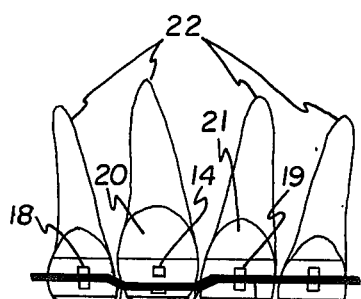
FIGS. 3A and 3D show second order (up and down) adjustments made on the arch wire with the pliers shown in FIGS. 1 and 2.
Figure 3D:
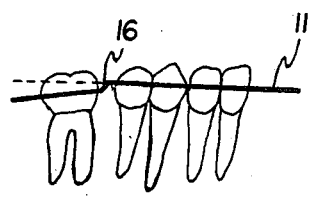
Figure 3B:
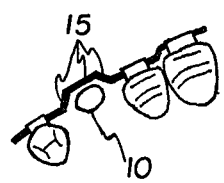
FIGS. 3B and 3C show a row of teeth with the arch wire attached to several of these teeth and first order (in or out) bends in said wire made by using the same pliers.
Figure 3C:
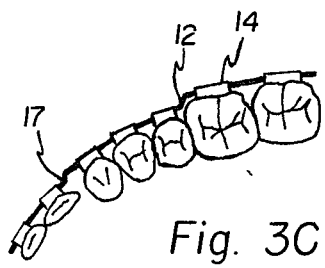

Regarding teeth 22, FIG. 3A shows a second order bend 13 while the arch wire 11 is detached from the bracket 14 but is still secured to the bracket 18 and bracket 19 to elevate tooth 20 in the same level a tooth 21. FIG. 3B shows a first order bend 15 to bypass a tooth 10 not completely erupted yet. FIG. 3C shows other first order bends 17 for a cuspid offset and a bayonet bend 12. FIG. 3D shows a second order bend 16 known as a tip back bend.

Figure 4A:
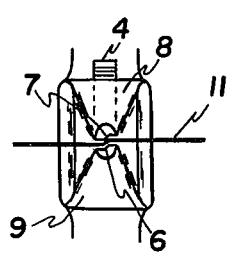
FIG. 4A is a front elevation of the pliers of FIG. 1 with an arch wire inserted in the pliers' jaw in the closed position.
Figure 4B:
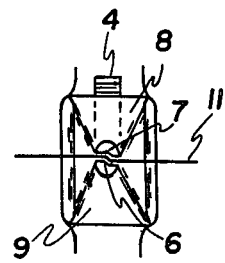
FIG. 4B is a front elevation of the pliers of FIG. 2 showing an arch wire in the jaws in the closed position.

FIG. 4A is a frontal elevation showing a set screw 4, arch wire 11 passing through the jaw, and beveled areas 7 and 6 of FIG. 1. FIG. 4B is a frontal elevation of the pliers of FIG. 2 showing the arch wire 11 passing through the beveled area 9 and having set screw 4 positioned in the upper jaw of the said pliers.

The setting of screw 4 determines the amount of closure of jaws 8 and 9, and thus the amount of bend the male portion 7 and female portion 6 will cause in forming the arch wire 11. As set screw 4 is positioned to impinge on platform 5, a bend of less than 45° will be achieved by the orthodontist on the arch wire 11. The amount of bend of arch wire 11 determines the tension of the bracket 14 of FIG. 3A, or bracket 10 of FIG. 3C.

The parameters of the pliers of this invention, namely, the step up or step down pliers as shown in FIGS. 1 and 2, are the following: A closed width of the jaws or beak of the pliers is approximately 2 mm. The beveled area at the 45° angle is approximately 1 mm. The width of the jaws is approximately 8 mm. Although these parameters are those found to be most useful when dealing with an arch wire of approximately 0.020-in. width, these dimensions are not critical but represent the preferred embodiment of this invention.

Whereas I have shown and described an operative form of my invention, I wish it to be understood that this showing and description thereof is to be taken in an illustrative or diagrammatic sense only. There are many modifications of the invention which will be apparent to those skilled in the art and which will fall within the spirit and scope of the invention. The scope of the invention should be limited only by the scope of the hereinafter appended claims.

What I claim is:
1. A set of two pliers for intra-oral wire bending, each of said pliers including:
   a. a pair of handles secured at and movable around a pivot means,
   b. a pair of jaws retained and movable by linkage members connected to and actuated by the movement of the handles so as to be movable in a parallel manner towards and away from each other, and
   c. hardened work surfaces formed in both the lower and upper jaw of said pliers, said surfaces containing male and female bevel portions being contoured to about a 45° angle.
2. The pliers of claim 1 in which said lower jaw contains:
   a. a platform portion formed adjacent to the pivot means, and
   b. in which said upper jaw contains an adjustable set screw which impinges on the platform of the said lower jaw and predetermines the spacing between said jaws when the handles are actuated to a closed position.

* * * * *